(12) United States Patent
Armacost et al.

(10) Patent No.: US 11,020,232 B2
(45) Date of Patent: Jun. 1, 2021

(54) DUAL MODULUS HIP STEM AND METHOD OF MAKING THE SAME

(71) Applicant: DEPUY SYNTHES PRODUCTS, INC., Raynham, MA (US)

(72) Inventors: John M. Armacost, Warsaw, IN (US);
Ryan C. Keefer, Warsaw, IN (US);
Jeffrey A. McAnelly, Columbia City, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 50 days.

(21) Appl. No.: 14/548,370

(22) Filed: Nov. 20, 2014

(65) Prior Publication Data
US 2015/0069111 A1    Mar. 12, 2015

Related U.S. Application Data

(62) Division of application No. 13/526,032, filed on Jun. 18, 2012, now Pat. No. 8,906,108.

(51) Int. Cl.
*A61F 2/30* (2006.01)
*A61F 2/36* (2006.01)
(Continued)

(52) U.S. Cl.
CPC .......... *A61F 2/3094* (2013.01); *A61F 2/3607* (2013.01); *A61F 2/3662* (2013.01);
(Continued)

(58) Field of Classification Search
CPC .... A61F 2/3662; A61F 2/3607; A61F 2/3094; A61F 2002/30014; A61F 2002/3011; A61F 2002/30405; A61F 2002/30919; A61F 2002/3092; A61F 2002/30968; A61F 2002/3631; A61F 2002/365; A61F 2002/3678; A61F 2310/00407; B23K 20/002; B23K 20/02; Y10T 29/49826
See application file for complete search history.

(56) References Cited

U.S. PATENT DOCUMENTS

| | | | |
|---|---|---|---|
| 4,351,069 A | | 9/1982 | Ballintyn et al. |
| 4,728,335 A | * | 3/1988 | Jurgutis .............. A61F 2/30734 623/23.23 |

(Continued)

FOREIGN PATENT DOCUMENTS

| | | | | |
|---|---|---|---|---|
| CA | 2354065 A1 | * | 11/1999 | ......... A61F 2/30767 |
| CA | 2299939 A1 | * | 9/2000 | ......... A61F 2/30767 |

(Continued)

OTHER PUBLICATIONS

Long, Marc et al., "Titanium alloys in total joint replacement—a materials science perspective," Biomaterials, 19, (1998), 1621-1639.

(Continued)

*Primary Examiner* — Christopher J Besler
(74) *Attorney, Agent, or Firm* — Barnes & Thornburg LLP (57) ABSTRACT

An orthopaedic prosthesis for use in a hip replacement surgery. The orthopaedic prosthesis includes a metallic foam shell and a metallic core. The metallic core includes a neck configured to receive a femoral head component and a stem extending through the metallic foam shell.

4 Claims, 6 Drawing Sheets

(51) Int. Cl.
  *B23K 20/00* (2006.01)
  *B23K 20/02* (2006.01)
  *B23K 1/00* (2006.01)

(52) U.S. Cl.
  CPC .......... *B23K 1/0008* (2013.01); *B23K 20/002* (2013.01); *B23K 20/02* (2013.01); *A61F 2002/30011* (2013.01); *A61F 2002/30014* (2013.01); *A61F 2002/3092* (2013.01); *A61F 2002/30405* (2013.01); *A61F 2002/30919* (2013.01); *A61F 2002/30968* (2013.01); *A61F 2002/30971* (2013.01); *A61F 2002/365* (2013.01); *A61F 2002/3631* (2013.01); *A61F 2002/3654* (2013.01); *A61F 2002/3678* (2013.01); *A61F 2310/00023* (2013.01); *A61F 2310/00029* (2013.01); *A61F 2310/00407* (2013.01); *A61F 2310/00413* (2013.01); *Y10T 29/49826* (2015.01)

(56) References Cited

U.S. PATENT DOCUMENTS

| | | | |
|---|---|---|---|
| 4,756,862 A | 7/1988 | Spector et al. | |
| 4,808,186 A | 2/1989 | Smith | |
| 4,851,008 A | 7/1989 | Johnson | |
| 4,878,919 A | 11/1989 | Pavlansky et al. | |
| 4,986,834 A | 1/1991 | Smith et al. | |
| 4,990,161 A | 2/1991 | Kampner | |
| 5,035,717 A * | 7/1991 | Brooks | A61F 2/30734 623/23.44 |
| 5,047,054 A * | 9/1991 | Vijayan | A61F 2/30767 623/23.6 |
| 5,169,597 A * | 12/1992 | Davidson | A61B 17/72 148/316 |
| 5,171,324 A * | 12/1992 | Campana | A61F 2/3662 606/86 R |
| 5,181,930 A | 1/1993 | Dumbleton et al. | |
| 5,236,457 A * | 8/1993 | Devanathan | A61F 2/30907 128/898 |
| 5,308,412 A * | 5/1994 | Shetty | A61F 2/30767 148/238 |
| 5,314,492 A | 5/1994 | Hamilton et al. | |
| 5,316,550 A | 5/1994 | Forte | |
| 5,336,265 A | 8/1994 | Serbousek et al. | |
| 5,433,750 A | 7/1995 | Gradinger et al. | |
| 5,443,513 A | 8/1995 | Moumene et al. | |
| 5,480,449 A | 1/1996 | Hamilton et al. | |
| 5,507,829 A * | 4/1996 | Thongpreda | A61F 2/30767 623/22.41 |
| 5,507,832 A * | 4/1996 | Michielli | A61F 2/30724 623/23.37 |
| 5,514,184 A | 5/1996 | Doi et al. | |
| 5,545,227 A | 8/1996 | Davidson et al. | |
| 5,549,702 A | 8/1996 | Ries et al. | |
| 5,549,705 A * | 8/1996 | Michielli | A61F 2/30734 623/23.37 |
| 5,571,187 A * | 11/1996 | Devanathan | A61F 2/30907 623/11.11 |
| 5,591,233 A | 1/1997 | Kelman et al. | |
| 5,702,448 A | 12/1997 | Buechel et al. | |
| 5,834,113 A | 11/1998 | Shalaby et al. | |
| 6,121,172 A | 9/2000 | Marcolongo et al. | |
| 6,228,123 B1 | 5/2001 | Dezzani | |
| 6,332,896 B1 * | 12/2001 | Hubbard | A61F 2/3662 623/23.24 |
| 6,409,852 B1 | 6/2002 | Lin et al. | |
| 6,464,728 B1 * | 10/2002 | Murray | A61F 2/30734 623/22.42 |
| 6,602,293 B1 | 8/2003 | Biermann et al. | |
| 6,626,948 B2 | 9/2003 | Storer et al. | |
| 6,656,226 B2 | 12/2003 | Yoon | |
| 6,695,884 B1 | 2/2004 | Townley | |
| 6,719,793 B2 | 4/2004 | McGee | |
| 6,887,278 B2 | 5/2005 | Lewallen | |
| 6,913,623 B1 | 7/2005 | Zhu | |
| 6,913,624 B2 * | 7/2005 | Hubbard | A61F 2/3662 623/23.15 |
| 7,141,073 B2 | 11/2006 | May et al. | |
| 7,214,246 B2 * | 5/2007 | Serbousek | A61F 2/367 623/23.15 |
| 7,842,096 B2 * | 11/2010 | Fridshtand | A61F 2/30767 623/22.11 |
| 7,947,084 B2 | 5/2011 | Link | |
| 8,088,169 B2 * | 1/2012 | Dorr | A61F 2/30767 623/23.32 |
| 8,206,455 B2 * | 6/2012 | Fridshtand | A61F 2/30767 623/22.11 |
| 8,252,062 B2 * | 8/2012 | Bandoh | A61F 2/30942 623/23.17 |
| 8,623,093 B2 * | 1/2014 | Dickerson | A61F 2/3607 623/19.11 |
| 8,858,646 B2 * | 10/2014 | Fridshtand | A61F 2/30767 623/23.24 |
| 8,906,108 B2 | 12/2014 | Armacost et al. | |
| 8,936,649 B2 * | 1/2015 | Huff | A61F 2/36 623/22.4 |
| 9,132,013 B2 * | 9/2015 | Armacost | A61F 2/3662 |
| 9,174,297 B2 * | 11/2015 | Vargas | A61F 2/30907 |
| 9,216,087 B2 * | 12/2015 | Dickerson | A61F 2/30734 |
| 2002/0049501 A1 | 4/2002 | Storer et al. | |
| 2002/0138151 A1 * | 9/2002 | Hubbard | A61F 2/3662 623/22.43 |
| 2004/0059427 A1 * | 3/2004 | Serbousek | A61F 2/367 623/22.29 |
| 2004/0172138 A1 | 9/2004 | May et al. | |
| 2005/0119759 A1 | 6/2005 | Tuke et al. | |
| 2005/0234560 A1 * | 10/2005 | Serbousek | A61F 2/367 623/23.24 |
| 2006/0190092 A1 * | 8/2006 | Fridshtand | A61F 2/30767 623/23.35 |
| 2006/0240064 A9 | 10/2006 | Hunter et al. | |
| 2007/0093912 A1 | 4/2007 | Borden | |
| 2007/0219641 A1 | 9/2007 | Dorr et al. | |
| 2008/0033568 A1 * | 2/2008 | Link | A61F 2/30767 623/22.4 |
| 2008/0039941 A1 | 2/2008 | Steinberg | |
| 2008/0167723 A1 | 7/2008 | Acker et al. | |
| 2008/0200990 A1 | 8/2008 | McTighe et al. | |
| 2008/0255675 A1 * | 10/2008 | Sidebotham | A61L 27/06 623/23.34 |
| 2008/0281430 A1 * | 11/2008 | Kelman | A61F 2/30734 623/23.23 |
| 2009/0005868 A1 * | 1/2009 | Gundlapalli | A61F 2/4644 623/11.11 |
| 2009/0187256 A1 * | 7/2009 | Rauguth | A61F 2/30767 623/23.55 |
| 2010/0312354 A1 * | 12/2010 | Bandoh | A61F 2/36 623/23.15 |
| 2011/0009973 A1 * | 1/2011 | Meyers | A61F 2/3607 623/20.32 |
| 2011/0035020 A1 | 2/2011 | Laughner | A61F 2/3094 623/22.4 |
| 2011/0190900 A1 * | 8/2011 | Link | A61F 2/367 623/22.4 |
| 2011/0257758 A1 * | 10/2011 | Smith | A61F 2/36 623/22.42 |
| 2012/0010720 A1 * | 1/2012 | Dickerson | A61F 2/30734 623/22.42 |
| 2012/0125896 A1 * | 5/2012 | Vargas | A61F 2/30907 219/108 |
| 2012/0221116 A1 * | 8/2012 | Fridshtand | A61F 2/30767 623/23.3 |
| 2013/0338789 A1 * | 12/2013 | Armacost | A61F 2/3662 623/23.34 |
| 2014/0039637 A1 * | 2/2014 | Dickerson | A61F 2/3607 623/22.4 |
| 2014/0094926 A1 * | 4/2014 | Huff | A61F 2/36 623/22.15 |

(56) References Cited

U.S. PATENT DOCUMENTS

| | | | |
|---|---|---|---|
| 2014/0107801 A1* | 4/2014 | Armacost | A61F 2/3662 623/22.42 |
| 2014/0277557 A1* | 9/2014 | Armacost | A61F 2/3662 623/22.15 |
| 2015/0025649 A1* | 1/2015 | Fridshtand | A61F 2/30767 623/23.35 |
| 2015/0069111 A1* | 3/2015 | Armacost | A61F 2/3662 228/101 |

FOREIGN PATENT DOCUMENTS

| | | | | |
|---|---|---|---|---|
| DE | 3442845 | A1 | 6/1985 | |
| FR | 2 839 641 | A1 | 11/2003 | |
| WO | WO 83/02555 | A1 | 8/1983 | |
| WO | 9306793 | A1 | 4/1993 | |
| WO | 200213730 | A2 | 2/2002 | |
| WO | WO 2008127658 | A1 * | 10/2008 | A61L 27/06 |
| WO | 2011005126 | A1 | 1/2011 | |

OTHER PUBLICATIONS

Machine Translation of French Patent Publication No. FR2839641 published on Nov. 21, 2003 as cited above, provided by the European Patent Office Espacenet Patent Search, http://worldwide.espacenet.com/advancedSearch?locale=en_EP, Aug. 12, 2014, 9 pages.

European Search Report, European Application No. 14197339.6-1654, completed Apr. 20, 2015, 6 pages.

\* cited by examiner

DUAL MODULUS HIP STEM AND METHOD OF MAKING THE SAME

The present application claims priority to U.S. patent application Ser. No. 13/526,032, now U.S. Pat. No. 8,906,108, which was filed on Jun. 18, 2012 and is expressly incorporated herein by reference.

TECHNICAL FIELD

The present disclosure relates generally to orthopaedic prostheses, and particularly to orthopaedic prostheses for use in hip replacement surgery.

BACKGROUND

Joint arthroplasty is a well-known surgical procedure by which a diseased and/or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes an elongated stem component that is received in the medullary canal of the patient's femur and a spherically-shaped head component that bears against the patient's acetabulum or a prosthetic replacement acetabular cup.

Many femoral prostheses are formed from metallic materials or a combination of metallic and polymeric materials. According to Wolff s law, a patient's bone tissue will remodel in proportion to the stress applied to it. Because elongated stem components formed from metal typically have an elastic modulus greater than the elastic modulus of the patient's bone, metallic stem components may shield the patient's bone from stress such that the proximal femoral bone does not remodel to an effective degree, possibly resulting in a loss of support for the implant and/or implant failures.

SUMMARY

According to one aspect of the disclosure, an orthopaedic prosthesis is disclosed. The orthopaedic prosthesis includes a metallic foam shell and a metallic core. The foam shell includes a sheath and a cover layer. The metallic core includes a neck positioned proximal of the sheath, the neck being configured to receive a femoral head component, a first core segment positioned in the sheath, and a second core segment positioned distal of the sheath. The cover layer of the foam shell extends distally from the sheath, and the cover layer engages only a lateral surface of the second core segment.

In some embodiments, the first core segment of the metallic core may have a medial surface and a lateral surface positioned opposite the medial surface. In some embodiments, the sheath may have a medial surface and a lateral surface positioned opposite the medial surface. Additionally, in some embodiments, when the orthopaedic prosthesis is viewed in a transverse plane, a first thickness may be defined between a medial-most point of the medial surface of the sheath and a medial-most point of the medial surface of the first core segment and a second thickness may be defined between a lateral-most point of the lateral surface of the sheath and a lateral-most point of the lateral surface of the first core segment. The first thickness may be less than the second thickness.

In some embodiments, the transverse plane may be a first transverse plane extending through the orthopaedic prosthesis between a proximal end of the sheath and a distal end of the sheath. When the orthopaedic prosthesis is viewed in a second transverse plane extending through the orthopaedic prosthesis at the distal end of the sheath, a third thickness may be defined between a medial-most point of the medial surface of the sheath and a medial-most point of the medial surface of the first core segment. The third thickness may be less than the first thickness.

In some embodiments, the third thickness may be less than 1.5 millimeters. Additionally, in some embodiments, when the orthopaedic prosthesis is viewed in the second transverse plane, a fourth thickness may be defined between a lateral-most point of the lateral surface of the sheath and a lateral-most point of the lateral surface of the first core segment. The fourth thickness may be greater than five millimeters.

In some embodiments, when the orthopaedic prosthesis is viewed in the second transverse plane, the medial surface of the first core segment may be convex, and the lateral surface of the first core segment may be convex. In some embodiments, when the orthopaedic prosthesis is viewed in the second transverse plane, the medial surface of the first core segment may be defined by a first radius, and the lateral surface of the first core segment may be defined by a second radius that is greater than the first radius.

Additionally, in some embodiments, the cover layer of the metallic foam shell may have a body that extends from a proximal end attached to the sheath to a distal end. The body may have a first thickness at the proximal end and a second thickness at the distal end. The second thickness may be less than the first thickness. In some embodiments, the first thickness of the body may be greater than three millimeters.

In some embodiments, the sheath of the metallic foam shell may have a porous outer surface. Additionally, in some embodiments, the cover layer of the metallic foam shell may have a non-porous outer surface.

In some embodiments, the metallic foam shell may have a first elastic modulus, and the metallic core may have a second elastic modulus. The first elastic modulus may be approximately one-twentieth of the second elastic modulus. In some embodiments, the metallic foam shell may be shaped to engage a surgically-prepared proximal end of a patient's femur. Additionally, in some embodiments, the first elastic modulus may be approximately one-tenth of the second elastic modulus. In some embodiments, the metallic foam shell may be shaped to engage a surgically-prepared proximal end of a patient's femur.

According to another aspect, an orthopaedic prosthesis includes a metallic foam shell having a first elastic modulus. The metallic foam shell has an outer surface that engages a patient's bony anatomy. The orthopaedic prosthesis also includes a metallic core including a neck positioned proximal of the shell and a body that extends through the shell. The core has a second elastic modulus greater than the first elastic modulus of the shell. When the orthopaedic prosthesis is viewed in a transverse plane extending through the shell and the core, a first thickness is defined between a medial-most point of the outer surface of the shell and a medial-most point of a medial surface of the core, and a second thickness is defined between a lateral-most point of the outer surface of the shell and a lateral-most point of a lateral surface of the core. The first thickness is less than the second thickness.

In some embodiments, the metallic core may be formed from a cobalt-chromium alloy. Additionally, in some embodiments, the metallic foam shell may be formed from titanium. In some embodiments, the metallic foam shell may be formed from a cobalt-chromium alloy. Additionally, in some embodiments, the metallic foam shell may be formed from titanium alloy.

In some embodiments, the body of the metallic core may include a first core segment coupled to the neck and positioned in the metallic foam shell and a second core segment positioned distal of the metallic foam shell. In some embodiments, the metallic foam shell may include a cover layer attached to only a lateral surface of the second core segment.

According to another aspect, a method of manufacturing an orthopaedic prosthesis for a patient is disclosed. The method includes producing a shell from a metallic foam material having a first elastic modulus, producing a stem core from a metallic material having a second elastic modulus greater than the first elastic modulus. The stem core includes a neck configured to receive a femoral head component. The method also includes securing the shell to the stem core such that the shell is positioned over a proximal segment of the stem core, and a cover layer of the shell extends along a lateral surface of a distal segment of the stem core.

In some embodiments, producing the shell may include forming a sheath over the proximal segment of the stem core such that the proximal segment of the stem core is encased therein. Additionally, in some embodiments, forming the sheath may include setting a medial thickness of the shell to between one millimeter and 1.5 millimeters at a distal end of the sheath.

In some embodiments, securing the shell to the core may include sintering the shell to the core. Additionally, in some embodiments, producing the shell from the metallic foam material may include compressing the metallic foam material around the stem core, and machining the metallic foam material to form the shell. In some embodiments, producing the shell from the metallic foam material may include compressing the metallic foam material to form an outer geometry of the shell, and machining a channel in the metallic foam material sized to receive the stem core.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
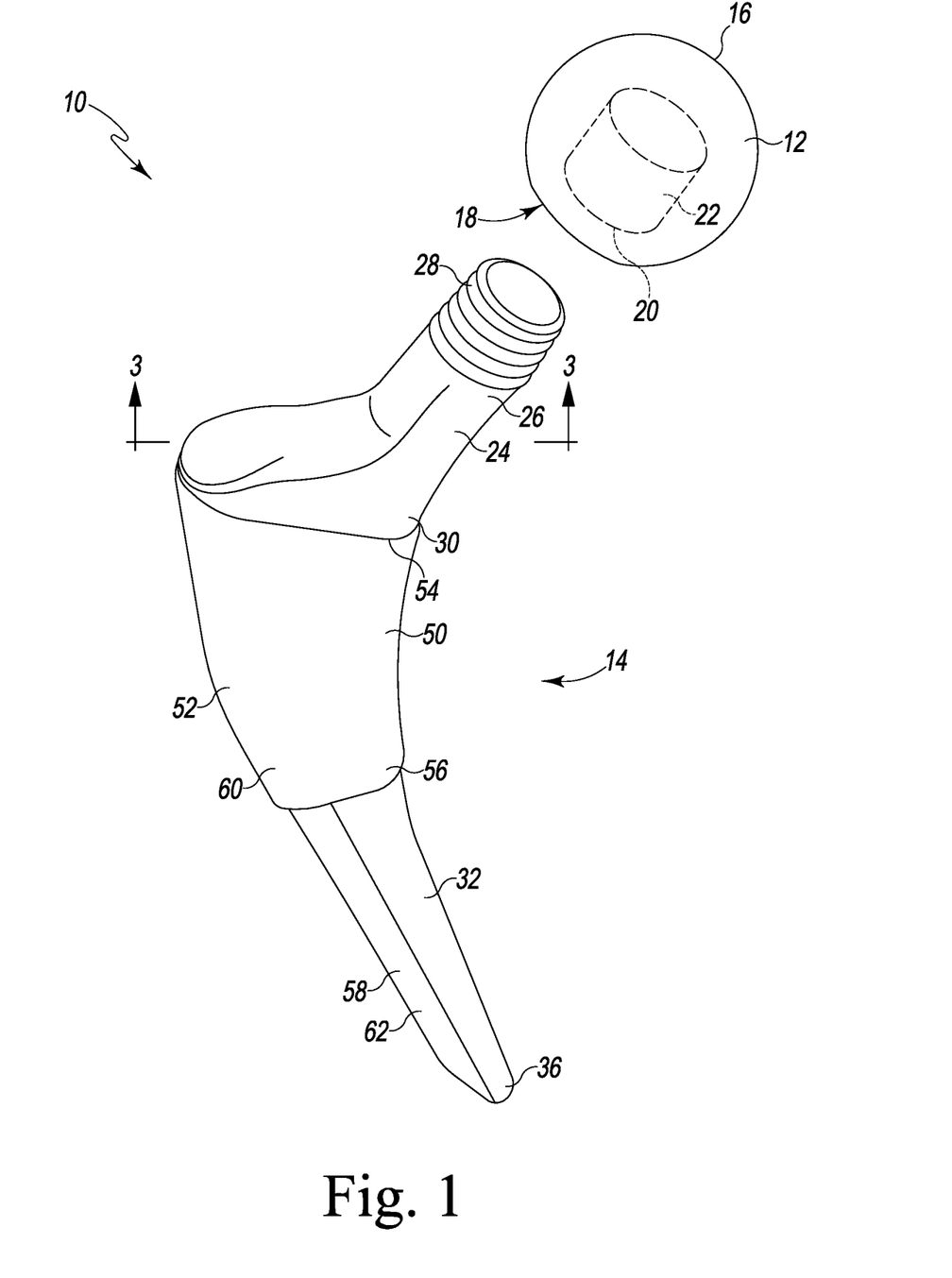
FIG. 1 is a perspective view of an orthopaedic implant.

Referring to FIG. 1, an orthopaedic prosthesis is illustratively embodied as a femoral orthopaedic implant 10 of a hip prosthesis. The femoral orthopaedic implant 10 (hereinafter implant 10) includes a head component 12 and an elongated stem component 14 that is configured to be inserted into an intramedullary canal of a patient's surgically-prepared femur (not shown). The head component 12 includes a spherical outer surface 16 configured to engage a patient's natural acetabulum (not shown) or a prosthetic acetabular cup implanted into the patient's pelvic bone. The head component 12 also includes a distal surface 18 having an opening 20 defined therein, and an inner wall (not shown) extends inwardly from the opening 20 to define an aperture 22 in the head component 12.

The stem component 14 of the implant 10 includes a core 24 having a neck 26 configured to be coupled to the head component 12. In the illustrative embodiment, the neck 26 includes a plurality of external threads 28 that are configured to engage with a plurality of internal threads (not shown) lining the aperture 22 of the head component 12. It should be appreciated that in other embodiments the neck and the head component may be configured to be press fit, taper fit, or secured together by other fastening means.

Figure 2:
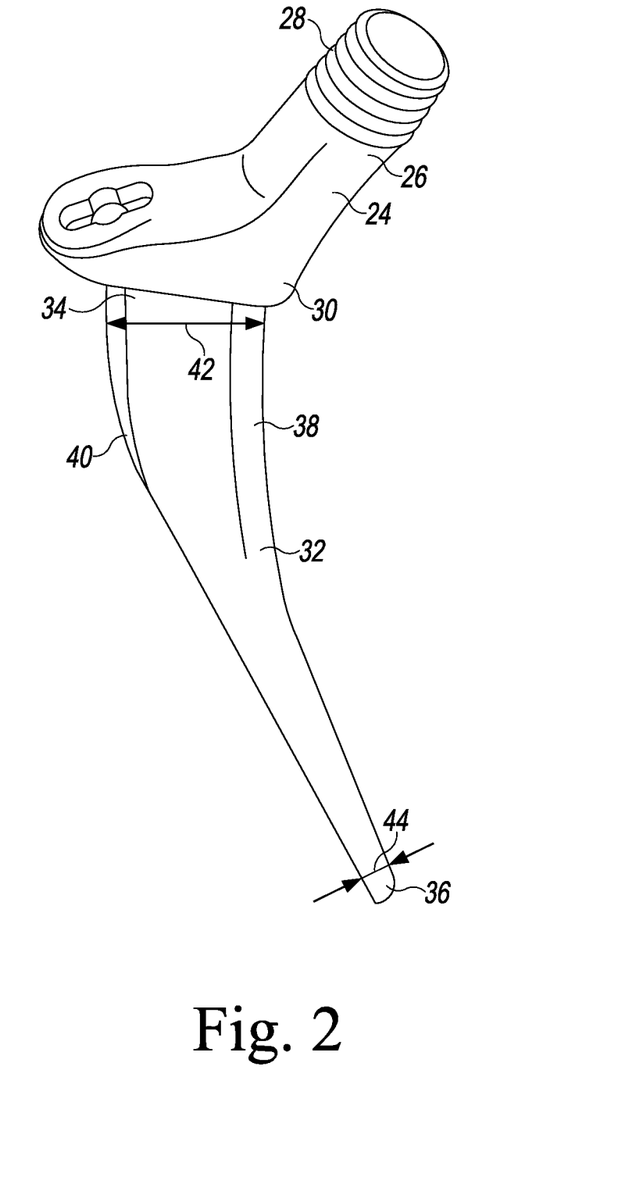
FIG. 2 is a perspective view of a core of the orthopaedic implant of FIG. 1.

As shown in FIG. 2, the core 24 of the stem component 14 also includes a collar 30 and a core body 32 extending distally from the collar 30. As shown in FIG. 1, the neck 26 extends medially and proximally from the collar 30. In the illustrative embodiment, the neck 26, the collar 30, and the core body 32 are formed as a monolithic structure (e.g., a single molded or cast part). It should be appreciated that in other embodiments the components of the core 24 (e.g., the neck 26, the collar 30, and the core body 32) may be formed as separate components secured to one another by a mechanical fastener (e.g., screw, bolt, taper fit, etc.), adhesive, or other suitable fastener.

The stem core 24 is formed from an implant grade metallic material having a high tensile strength and a high elastic modulus (i.e., a high material stiffness). As used herein, the term "high tensile strength" refers to a tensile strength that is greater than 650 MPa. Additionally, as used herein, the term "high elastic modulus" refers to an elastic modulus or modulus of elasticity that is greater than or equal to 100 GPa. In the illustrative embodiment, the core 24 is formed from cobalt-chromium alloy ("CoCr") having a minimum ultimate tensile strength of 650 MPa and an elastic modulus of approximately 195 GPa. It should be appreciated that in other embodiments the core 24 may be formed from any material having a high tensile strength and a high elastic modulus, including, for example, a titanium alloy such as Ti-6Al-4V, which has a minimum ultimate tensile strength of 750 MPa and an elastic modulus of approximately 105 GPa.

As described above, the core 24 of the stem component 14 includes a core body 32, which lies generally in the coronal plane of a patient's body when the implant 10 is secured to the patient's femur. As shown in FIG. 2, the core body 32 of the core 24 extends from a proximal end 34 attached to the collar 30 to a distal end 36. The core body 32 includes a medial surface 38 and a lateral surface 40 positioned opposite the medial surface 38. When the core 24 of the stem component 14 is viewed in the coronal plane, the core body 32 has a thickness 42 at the proximal end 34, which is defined between the surfaces 38, 40 of the core body 32. The core body 32 has another thickness 44 defined between the surfaces 38, 40 at the distal end 36. In the illustrative embodiment, the thickness 44 is less than the thickness 42, and the core body 32 tapers to decrease in thickness between the proximal end 34 and the distal end 36.

In the illustrative embodiment, the medial surface 38 of the core body 32 is convex. As described in greater detail below, the medial surface 38 is defined by a radius 46 (see FIGS. 4-7) that decreases in magnitude as the medial surface 38 extends from the proximal end 34 of the core body 32 to the distal end 36. The lateral surface 40 is also convex in the illustrative embodiment. The lateral surface 40, like the medial surface 38, is defined by a radius 48 (see FIGS. 4-7) that decreases in magnitude as the lateral surface 40 extends from the proximal end 34 of the core body 32 to the distal end 36. While the radii 46, 48 decrease in magnitude, the magnitude of the radius 48 of the lateral surface 40 is greater than the magnitude of the radius 46 of the medial surface 38.

Returning to FIG. 1, the stem component 14 of the implant 10 also includes a shell 50 that is secured to the core 24. The shell 50 has a sheath 52 that has a proximal end 54 attached to the collar 30 and a distal end 56 positioned between the collar 30 and the distal end 36 of the core 24. The shell 50 also includes a cover layer 58 that extends distally from the sheath 52 to the distal end 36 of the core body 32. In the illustrative embodiment, the sheath 52 and the cover layer 58 are formed as a monolithic structure. It should be appreciated that in other embodiments the components of the shell 50 (e.g., sheath 52 and the cover layer 58) may be formed as separate components. The separate components may be secured to one another by a mechanical fastener (e.g., screw, bolt, taper fit, etc.), adhesive, or other suitable fastener or secured separately to the core 24.

The shell 50 of the stem component 14 is formed from a metallic foam matrix having a low elastic modulus. As used herein, a "low elastic modulus" refers to an elastic modulus or modulus of elasticity similar to that of a patient's natural femur (i.e., between 10 GPa and 20 GPa). In the illustrative embodiment, the shell 50 is formed from a foam matrix of titanium having an elastic modulus of approximately 10 GPa and an ultimate tensile strength of the foam matrix of titanium is approximately 35 MPa. In that way, the shell 50 has an elastic modulus that is closer to that of a patient's femur. It should be appreciated that in other embodiments the shell 50 may be formed any metallic foam matrix having a low elastic modulus, such as, for example, a CoCr foam matrix having an elastic modulus of approximately 19 GPa, a CoCr alloy foam matrix, a titanium foam alloy matrix, or other foam matrix.

As described above, the core 24 of the stem component 14 in the illustrative embodiment is formed from CoCr having an elastic modulus of approximately 195 GPa while the shell 50 is formed from a foam matrix of titanium having an elastic modulus of approximately 10 GPa. Thus, in the illustrative embodiment, the elastic modulus of the shell 50 is approximately ¹⁄₂₀ of the elastic modulus of the core 24. In still other embodiments, the core may be formed from CoCr having an elastic modulus of approximately 195 GPa and the shell may be formed from a CoCr foam matrix having an elastic modulus of approximately 19 GPa. In such embodiments, the elastic modulus of the shell is approximately ¹⁄₁₀ of the elastic modulus of the core. In other embodiments, the core may be formed from Ti-6 Al-4V having an elastic modulus of approximately 105 GPa and the shell may be formed from a titanium foam matrix having an elastic modulus of approximately 10 GPa. In such embodiments, the elastic modulus of the shell is approximately ¹⁄₁₀ of the elastic modulus of the core.

As shown in FIG. 1, the sheath 52 of the shell 50 has an outer surface 60, and the cover layer 58 has an outer surface 62. The outer surfaces 60, 62 define a portion of the external geometry of the implant 10. As such, the outer surfaces 60, 62 engage the portion of the patient's femur defining the intramedullary canal when the implant 10 is inserted into the proximal end of the patient's surgically-prepared femur. In the illustrative embodiment, the outer surface 60 of the sheath 52 is porous to enable bone ingrowth fixation, and the outer surface 62 of the cover layer 58 is non-porous. It should be appreciated that in other embodiments the cover layer 58 may also be porous.

Figure 3:
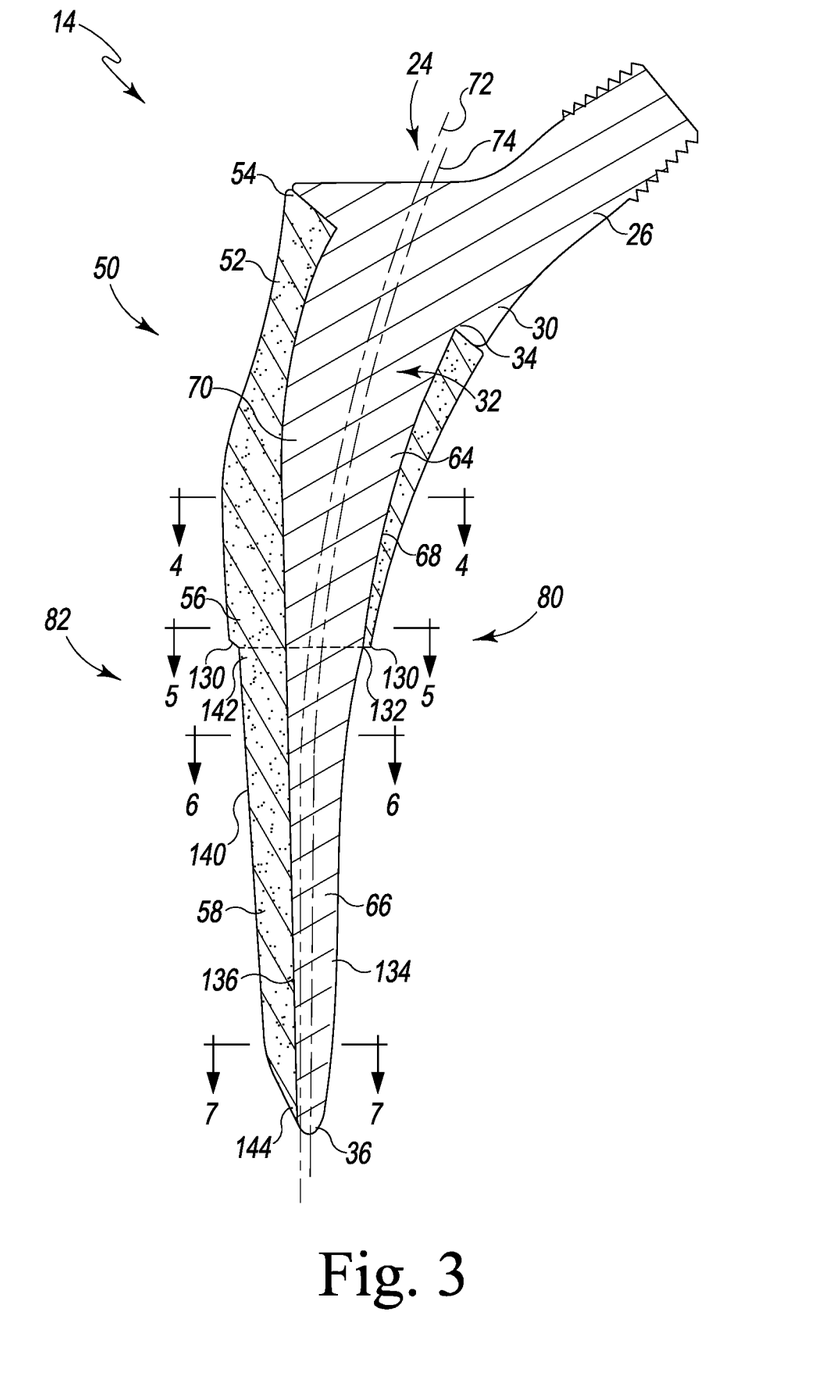
FIG. 3 is a cross-sectional view of the orthopaedic implant taken along the line 3-3 in FIG. 1.

As shown in FIG. 3, the core body 32 of the stem core 24 extends through the sheath 52 of the shell 50. The core body 32 includes a core segment 64 that is positioned in the sheath 52, and a core segment 66 that is positioned distal of the sheath 52. The sheath 52 is attached to and encases a medial surface 68 and a lateral surface 70 of the core segment 64. The surfaces 68, 70 form proximal sections of the medial surface 38 and lateral surface 40, respectively, of the core body 32.

The core body 32 (i.e., the core segments 64, 66) and the shell 50 (i.e., the sheath 52 and cover layer 58) cooperate to define a longitudinal axis 72 of the stem component 14, which extends between the proximal end 34 and the distal end 36. The core body 32 has a longitudinal axis 74 that is defined between the ends 34, 36, and the axis 74 is offset from the axis 72. In the illustrative embodiment, the axis 74 is offset in the medial direction from the axis 72 such that the core body 32 is biased toward the medial side 80 of the stem component 14 and away from the lateral side 82 of the stem component 14. Additionally, the thickness of the shell 50 on the lateral side 82 of the stem component 14 is greater than the thickness of the shell 50 on the medial side 80 of the stem component 14.

Figure 4:
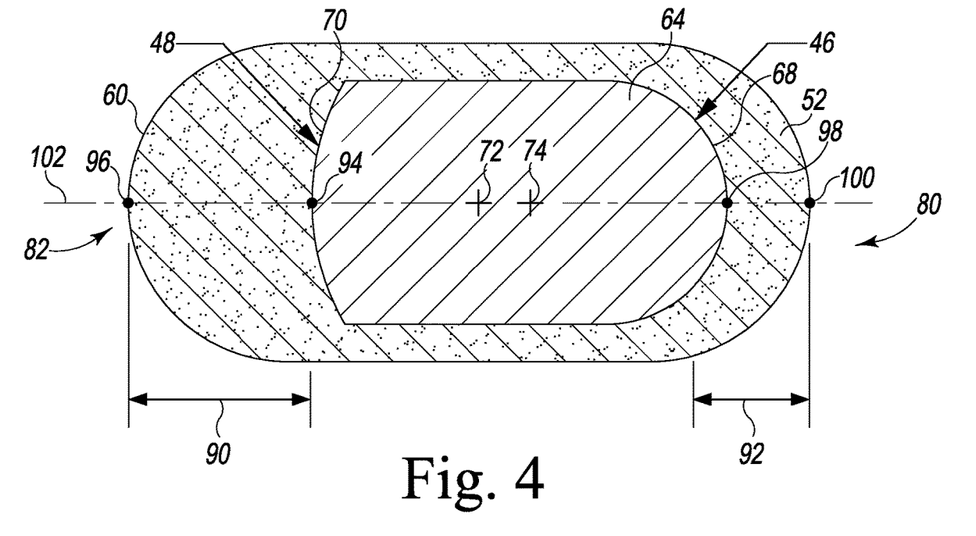
FIG. 4 is a cross-sectional view of the orthopaedic implant taken along the line 4-4 in FIG. 3.

For example, as shown in FIG. 4, the sheath 52 has a lateral thickness 90 and a medial thickness 92 when viewed in a transverse plane extending through the stem component 14 between the proximal end 54 and the distal end 56 of the sheath 52. The lateral thickness 90 of the sheath 52 is defined between a lateral-most point 94 of the lateral surface 70 of the core segment 64 and a lateral-most point 96 of the outer surface 60 of the sheath 52. The medial thickness 92 of the sheath 52 is defined between a medial-most point 98 of the medial surface 68 of the core segment 64 and a lateral-most point 100 of the outer surface 60 of the sheath 52. Each of the points 94, 96, 98, 100 lies in the coronal plane, as indicated by an imaginary line 102.

As shown in FIG. 4, the lateral thickness 90 is greater than the medial thickness 92. In other words, the thickness 90 of the shell 50 on the lateral side 82 of the stem component 14 is greater than the thickness 92 of the shell 50 on the medial side 80 of the stem component 14. In the illustrative embodiment, the lateral thickness 90 is greater than 5 millimeters, and the medial thickness 92 is between 2 and 4.5 millimeters.

Figure 5:
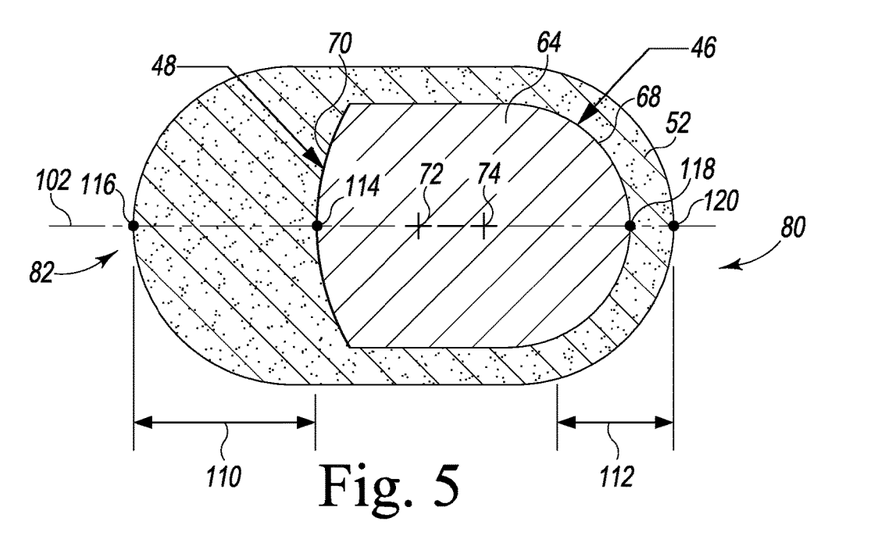
FIG. 5 is a cross-sectional view of the orthopaedic implant taken along the line 5-5 in FIG. 3.

As shown in FIGS. 3-5, the thickness of the sheath 52 of the shell 50 on the medial side 80 of the stem component 14 generally decreases from the proximal end 54 and the distal end 56 of the sheath 52. As shown in FIG. 5, the sheath 52 has a lateral thickness 110 and a medial thickness 112 when viewed in a transverse plane extending through the stem component 14 at the distal end 56 of the sheath 52. The lateral thickness 110 of the sheath 52 is defined between a lateral-most point 114 of the lateral surface 70 of the core segment 64 and a lateral-most point 116 of the outer surface 60 of the sheath 52. The medial thickness 112 of the sheath 52 is defined between a medial-most point 118 of the medial surface 68 of the core segment 64 and a lateral-most point 120 of the outer surface 60 of the sheath 52. Each of the points 114, 116, 118, 120 lies in the coronal plane, as indicated by the imaginary line 102.

As shown in FIG. 5, the lateral thickness 110 of the sheath 52 is again greater than the medial thickness 112 of the sheath 52. In the illustrative embodiment, the lateral thickness 10 is greater than five millimeters. Additionally, the medial thickness 112 at the distal end 56 of the sheath 52 is less than the medial thickness 92, which is shown in FIG. 4 between the proximal end 54 and the distal end 56 of the sheath 52. As described above, the medial thickness 92 of sheath 52 in the illustrative embodiment is between 2 and 4.5 millimeters, and, in the illustrative embodiment, the medial thickness 112 of the sheath 52 is between 1 and 1.5 millimeters.

Returning to FIG. 3, the outer surface 60 of the sheath 52 has a curved or rounded distal surface section 130 at the distal end 56 of the sheath 52. The distal surface section 130 has an edge 132 that extends around the core body 32 of the stem core 24 and the cover layer 58 of the shell 50. As described above, the core body 32 also includes a core segment 66 that is positioned distal of the end 56 of the sheath 52. The core segment 66 extends from the edge 132 of the sheath 52 to the distal end 36 of the core body 32.

The core segment 66 has a medial surface 134 that forms a distal section of the medial surface 38 of the core body 32. The core segment 66 also has a lateral surface 136 that forms a distal section of the lateral surface 40 of the core body 32. As shown in FIG. 3, the cover layer 58 of the shell 50 is attached to only the lateral surface 136 of the core segment 66. The medial surface 134 of the core segment 66, like the shell 50, forms a portion of the external geometry of the implant 10 such that the medial surface 134 may engage the patient's bone when the implant 10 is inserted into the intramedullary canal.

Figure 6:
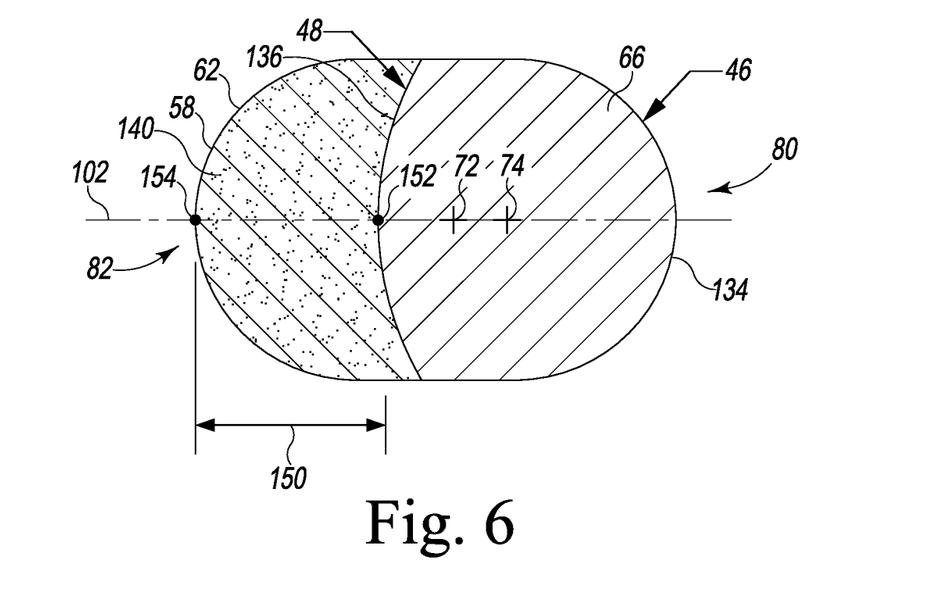
FIG. 6 is a cross-sectional view of the orthopaedic implant taken along the line 6-6 in FIG. 3.

As shown in FIG. 3, the cover layer 58 has a body 140 that extends from a proximal end 142 attached to the sheath 52 to a distal end 144 secured to the distal end 36 of the core body 32. In the illustrative embodiment, the thickness of the body 140 decreases between the ends 142, 144. For example, as shown in FIG. 6, the body 140 has a lateral thickness 150 when viewed in a transverse plane that extends through the stem component 14 between the ends 142, 144 of the cover layer 58. The lateral thickness 150 of the body 140 is defined between a lateral-most point 152 of the lateral surface 136 of the core segment 66 and a lateral-most point 154 of the outer surface 62 of the cover layer 58. As shown in FIG. 6, the lateral thickness 150 is greater than 4.5 millimeters.

Figure 7:
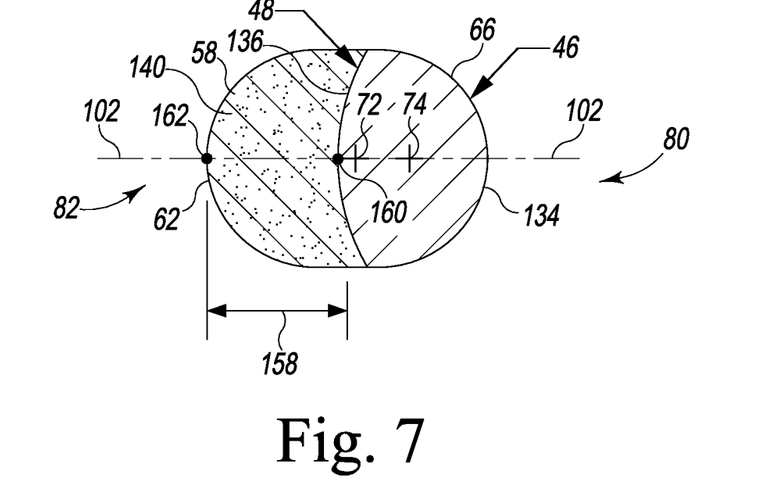
FIG. 7 is a cross-sectional view of the orthopaedic implant taken along the line 7-7 in FIG. 3.

As shown in FIG. 7, the body 140 has a lateral thickness 158 when viewed in a transverse plane extending through the stem component 14 at the distal end 144 of the cover layer 58. The lateral thickness 158 of the body 140 is defined between a lateral-most point 160 of the lateral surface 136 of the core segment 66 and a lateral-most point 162 of the outer surface 62 of the cover layer 58. In the illustrative embodiment, the lateral thickness 158 of the body 140 is between 4 millimeters and 3 millimeters. In other words, the lateral thickness 158 of the body 140 at the distal end 144 of the cover layer 58 is less than the lateral thickness 150 of the body 140 between the ends 142, 144.

In use, the implant 10 is inserted into a proximal end of a patient's surgically-prepared femur. The elongated stem component 14 is received in the intramedullary canal and the sheath 52 and the cover layer 58 of the shell 50 engage the portion of the patient's femur surrounding the canal. The core 24 is sized and shaped to meet the minimum strength requirements of the implant 10, while the shell 50 is configured to possess the external geometry necessary to fit into the intramedullary canal. The combination of the high tensile strength/high elastic modulus core 24 with the low modulus shell 50 results in a reduced stiffness for the implant 10 such that stress shielding of the patient's bone is reduced.

Figure 8:
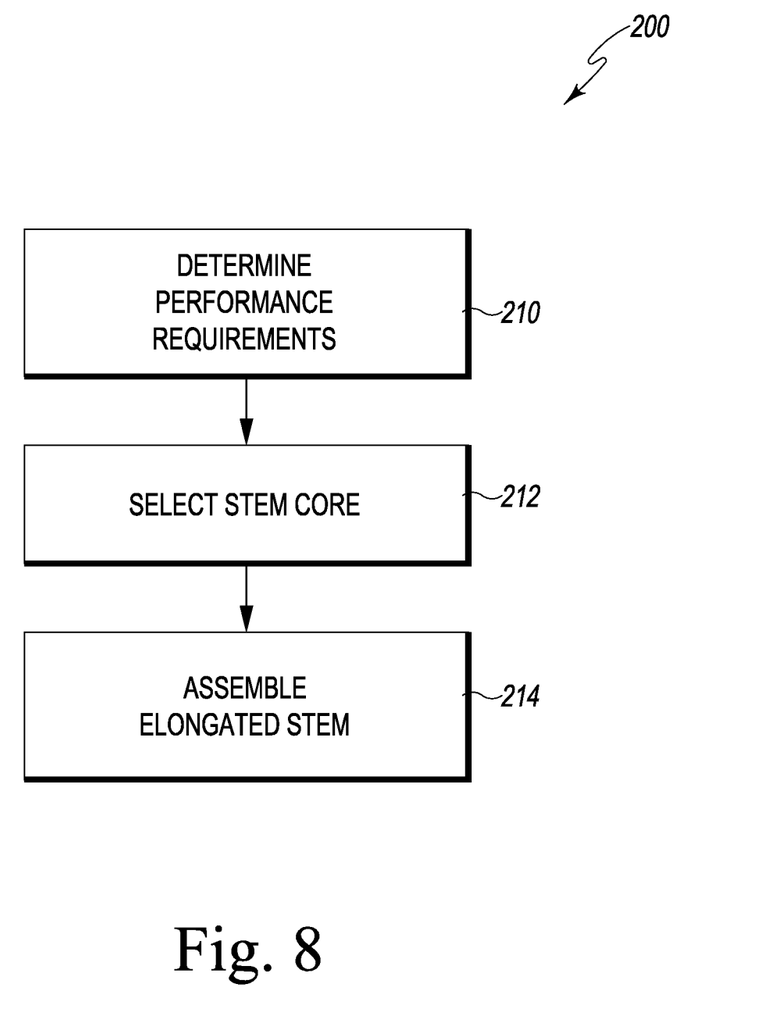
FIG. 8 is a simplified block diagram of a process for manufacturing the orthopaedic implant of FIGS. 1-7.

Referring now to FIG. 8, a method 200 of manufacturing the elongated stem component 14 of the implant 10 is illustrated. In the illustrative method, the performance requirements of the stem component 14 are determined and the stem core 24 of the stem component 14 is procured. The stem core 24 and the shell 50 may then be assembled to form the stem component 14.

In block 210, the performance requirements of the stem component 14 are determined. The performance requirements for the stem component 14 may vary between different patients such that a customized stem component 14 may be required. The performance requirements include the external geometry and the minimum endurance and performance requirements, such as, for example, the minimum tensile strength and the minimum stiffness of the stem component 14.

In block 212, the core 24 of the stem component 14 is selected. The core 24 may be an off-the-shelf, generic core that may be used with multiple implant sizes. The core 24 may be a customized, patient-specific component designed to satisfy the performance requirements of a particular patient. Whether the core 24 is generic or custom, the selected core 24 of the component 14 is sized and shaped to provide the minimum strength of the implant 10. The minimum strength of the core 24 is determined in accordance with International Organization for Standardization Standard No. 7206-4:2010 "IMPLANTS FOR SURGERY—PARTIAL AND TOTAL HIP JOINT PROSTHESES—PART 4: DETERMINATION OF ENDURANCE PROPERTIES AND PERFORMANCE OF STEMMED FEMORAL COMPONENTS" and Standard No. 7206-6: 1992 "IMPLANTS FOR SURGERY—PARTIAL AND TOTAL HIP JOINT PROSTHESES—PART 6: DETERMINATION OF ENDURANCE PROPERTIES OF HEAD AND NECK REGION OF STEMMED FEMORAL COMPONENTS."

In block 214, the stem component 14 is assembled. To do so, a metallic foam matrix, which will form the shell 50 of the stem component 14, is procured. The metallic foam matrix may be compressed around the core 24 such that the core 24 is received in a channel within the foam matrix. The foam matrix may then be machined to the required external geometry of the shell 50. Alternatively, the metallic foam matrix may be compressed separately into the shape of shell 50. After the matrix is compressed, a channel sized to receive the core 24 may be machined in the shell 50 before the shell 50 is assembled with the core 24.

A sintering operation may be used to secure the shell 50 to the core 24. It should also be appreciated that the shell 50 and the core 24 may be secured via a brazing operation, a press-fit, or other securing means.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of manufacturing an orthopaedic prosthesis for a patient, comprising:
   producing a shed from a metallic foam material having a first elastic modulus,
   producing a stem core from a metallic material having a second elastic modulus greater than the first elastic modulus, the stem core including a neck configured to receive a femoral head component, a collar, and a stem body that extends from the collar to a distal tip, the stem body comprising a proximal segment that extends distally from the collar and a distal segment that extends distally from a distal end of the proximal segment to the distal tip, and
   securing the shell to the stem body such that (i) the shell completely encases the proximal segment of the stem body, (ii) the shell covers a lateral surface of the distal segment of the stem body from the distal end of the proximal segment through an area adjacent the distal tip, and (iii) a medial surface of the distal segment of the stem body from the distal end of the proximal segment through the area adjacent the distal Up is devoid of the shell.

2. The method of claim 1, wherein securing the shell to the stem body includes sintering the shell to the stem body.

3. The method of claim 1, wherein producing the shell from the metallic foam material includes:
   compressing the metallic foam material around the stem core, and
   machining the metallic foam material to form the shell.

4. The method of claim 1, wherein producing the shell from the metallic foam material includes:
   compressing the metallic foam material to form an outer geometry of the shell, and
   machining a channel in the metallic foam material sized to receive the stem core.

\* \* \* \* \*